United States Patent [19]
Lay

[11] Patent Number: 5,772,617
[45] Date of Patent: Jun. 30, 1998

[54] STABILIZING ARM SLING

[75] Inventor: Bonnita S. Lay, Gardner, Kans.

[73] Assignee: A&B Stablizer, Inc., Olathe, Kans.

[21] Appl. No.: 731,092

[22] Filed: Oct. 9, 1996

[51] Int. Cl.⁶ ...................................................... A61F 5/00
[52] U.S. Cl. .................................. 602/4; 602/62; 128/878
[58] Field of Search ............................... 602/4, 5, 60–62, 602/19; 128/877, 878; 224/671, 673, 625, 637, 664, 204, 606

[56] References Cited

U.S. PATENT DOCUMENTS

| | | | |
|---|---|---|---|
| 3,515,131 | 6/1970 | Stevens | 602/4 |
| 3,780,729 | 12/1973 | Garnett | 602/4 |
| 4,355,635 | 10/1982 | Bihl et al. . | |
| 4,372,301 | 2/1983 | Hubbard . | |
| 4,390,014 | 6/1983 | Forman | 602/19 |
| 4,598,702 | 7/1986 | Lilla . | |
| 4,625,719 | 12/1986 | Chambers | 602/4 |
| 4,751,923 | 6/1988 | Marino | 602/4 |
| 4,759,353 | 7/1988 | Melendez et al. . | |
| 4,924,557 | 5/1990 | Heckerman et al. | 24/16 PB |
| 5,009,348 | 4/1991 | Derkatz | 224/232 |
| 5,334,132 | 8/1994 | Burkhead . | |
| 5,358,470 | 10/1994 | Johnson | 602/62 |
| 5,413,552 | 5/1995 | Iwuala . | |
| 5,464,383 | 11/1995 | Padden et al. . | |
| 5,511,704 | 4/1996 | Linderer | 224/245 |

*Primary Examiner*—Richard J. Apley
*Assistant Examiner*—Denise Pothier
*Attorney, Agent, or Firm*—Litman, McMahon & Brown, LLC

[57] ABSTRACT

An arm sling comprises a sling pouch in which a retaining strap or belt is secured to a back panel of the sling pouch intermediate the ends of the sling pouch. The restraining strap is secured to the back panel intermediate the ends of the restraining strap and preferably at two points or along two sets of stitches. Opposite ends of the restraining strap are removably securable together by a fastener such that the restraining strap may be readily secured around the torso of the wearer with the sling pouch and the arm therein being held against the wearer's abdomen without pulling on the ends of the sling pouch. The restraining strap is preferably secured to the back panel at a slight angle, approximately five degrees, relative to a bottom edge thereof and from a wrist end to an elbow end of the sling pouch to support the wrist in a slightly elevated orientation relative to the elbow when the sling is donned. A shoulder strap connected to a front end and rear end of the sling pouch provides additional support for the sling pouch and the arm.

17 Claims, 2 Drawing Sheets

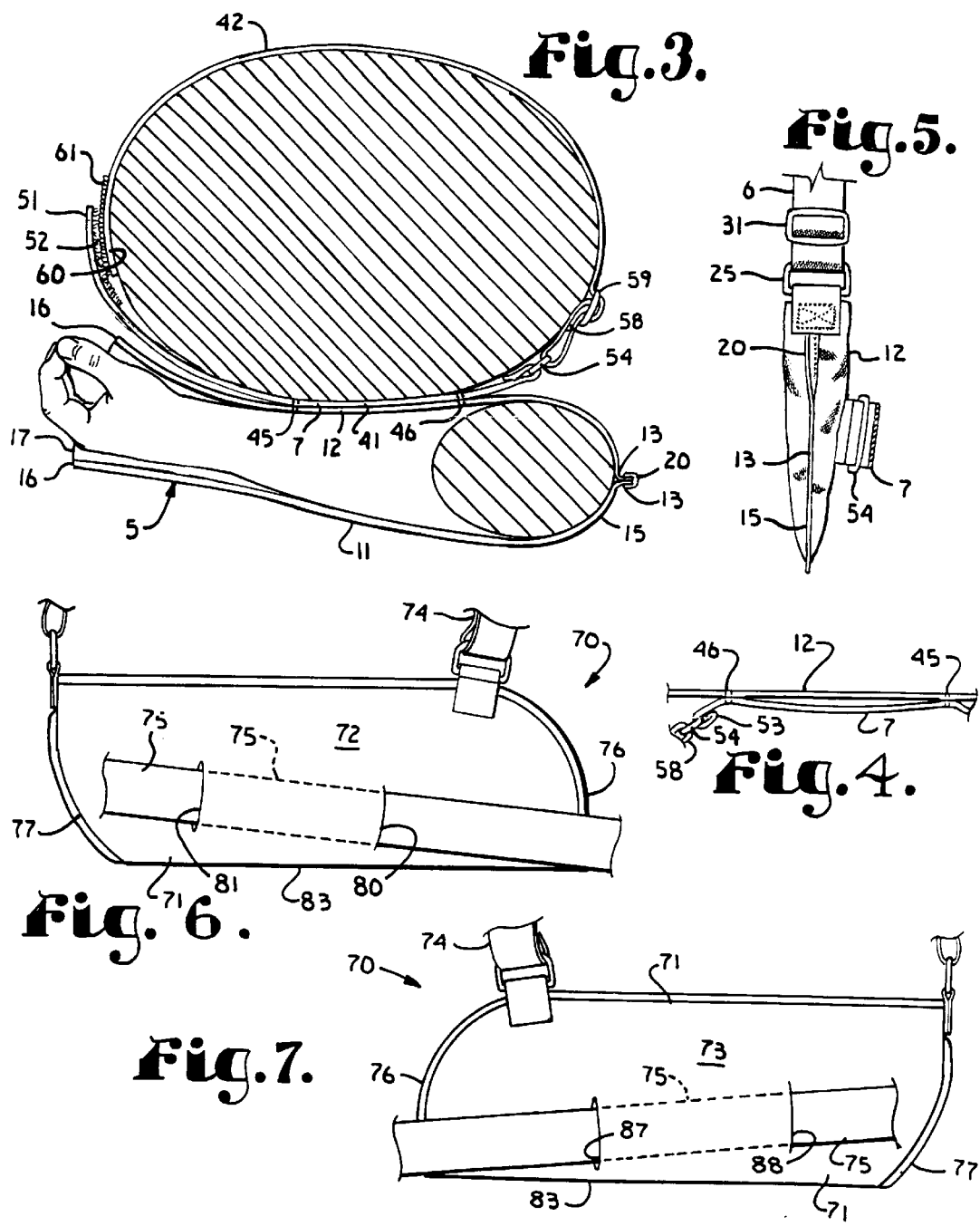

5,772,617

STABILIZING ARM SLING

BACKGROUND OF THE INVENTION

1. Field of the Invention

The present invention relates to arm slings for comfortably supporting and immobilizing the wearer's arm.

2. Prior Art

Many attempts have been made to provide stabilizing arm slings which comfortably support the wearer's arm and which hold the sling against the body to limit unintentional movement of the arm and/or the shoulder. Early attempts at securing slings against the body involved extending and securing a separate belt across an outer surface of the sling, around the upper arm of the arm to be immobilized and under the opposite arm. Such an arrangement often proved uncomfortable and difficult to attach.

U.S. Pat. No. 4,372,301 shows another common method of securing the arm sling against the body in which opposite ends of a restraining strap are secured to a front end and a rear end of a sling pouch respectively. When the arm, in the sling pouch, is positioned against the abdomen, the arm typically does not rest completely flush against the abdomen. Both the elbow and the wrist and hand generally extend tangentially away from the abdomen and are spaced away from the wearer's sides. When the restraining strap is tightened down to secure the sling pouch and arm against the abdomen, the tension of the strap on the sling pouch and the arm therein produces an uncomfortable strain on the arm at the elbow and the wrist.

There remains a need for a stabilizing arm sling which comfortably secures an arm in the sling against the body and which is easy to put on and adjust.

SUMMARY OF THE INVENTION

The present invention comprises an arm sling having a sling pouch in which a retaining strap is secured to a back panel of the sling pouch intermediate the ends of the sling pouch. The restraining strap is secured to the back panel intermediate the ends of the restraining strap and preferably at two points. Opposite ends of the restraining strap are removably securable together by a fastener such that the restraining strap may be readily secured around the torso of the wearer with the sling pouch and the arm therein being held against the wearer's abdomen without pulling on the ends of the sling pouch. A shoulder strap connected to a front end and rear end of the sling pouch provides additional support for the sling pouch and the arm.

The fastener used to secure the ends of the restraining strap together preferably is of a type which permits adjustments in the circumference of the loop extending around the wearer's waist to facilitate obtaining a snug but comfortable fit. The shoulder strap is secured to the sling pouch by means for readily permitting adjustment of the length of the shoulder strap.

The restraining strap is secured to the back panel of the sling pouch at a upwardly inclined angle from a front end to a rear end of the sling pouch such that when the restraining strap is secured around a wearer's torso the front end of the sling pouch and therefore the wearer's wrist is supported higher than the wearer's elbow. Such an orientation is generally more comfortable for the wearer.

OBJECTS AND ADVANTAGES OF THE INVENTION

Therefore the objects of this invention include to provide an arm sling which comfortably immobilizes the wearer's arm and shoulder; to provide such a sling which holds the wearer's arm against their abdomen; to provide such a sling which holds the wearer's arm against their abdomen without placing uncomfortable strain on the wearer's wrist and elbow; to provide such a sling which is readily adjustable to fit a wide variety of sizes and to achieve a proper and comfortable fit; to provide such a sling which is easy to don; to provide such a sling which the wearer may put on without assistance; to provide such a sling which is easy and relatively inexpensive to manufacture and to provide such a sling which is particularly well adapted for its intend purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 3 is an enlarged cross-sectional view taken generally along line 3—3 of FIG. 1.

FIG. 4 is an enlarged and fragmentary cross-sectional view taken generally along line 4—4 of FIG. 2.

FIG. 5 is an enlarged and fragmentary view taken generally along line 5—5 of FIG. 2.

FIG. 6 is fragmentary view of an alternative embodiment of the present invention showing a restraining strap extending through slits in a first panel of a sling pouch.

FIG. 7 is a view similar to FIG. 6 showing the restraining strap extending through slits in a second panel of the sling pouch shown in FIG. 6.

DETAILED DESCRIPTION OF THE INVENTION

Figure 1:
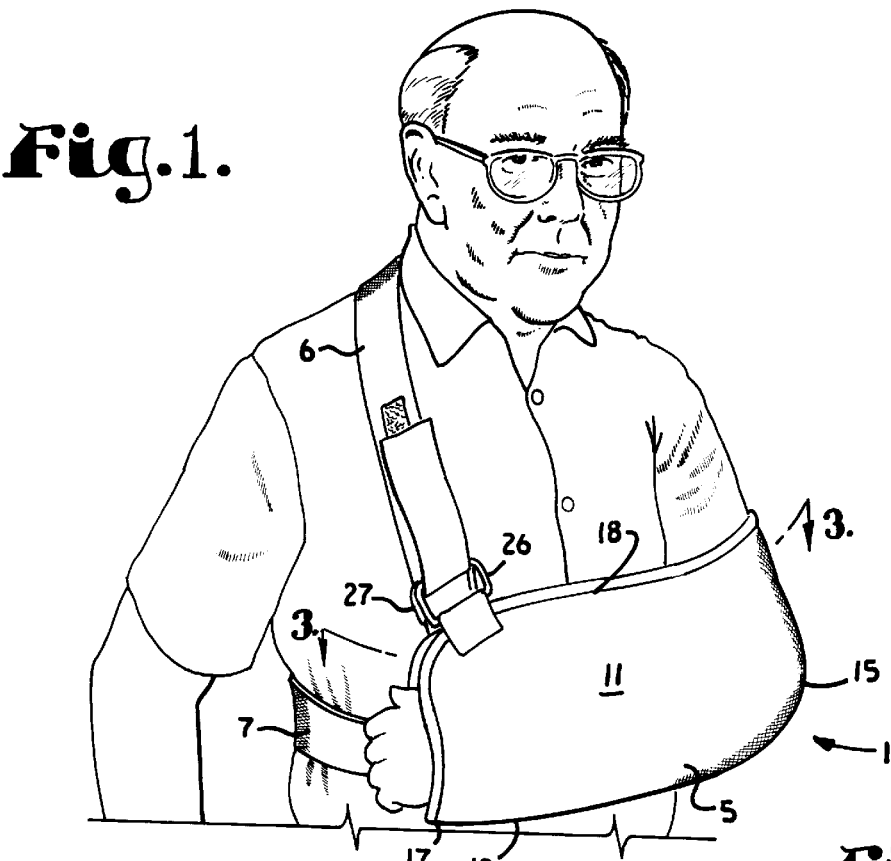
FIG. 1 is a perspective view of an arm sling of the present invention supporting an arm of a wearer.
Figure 2:
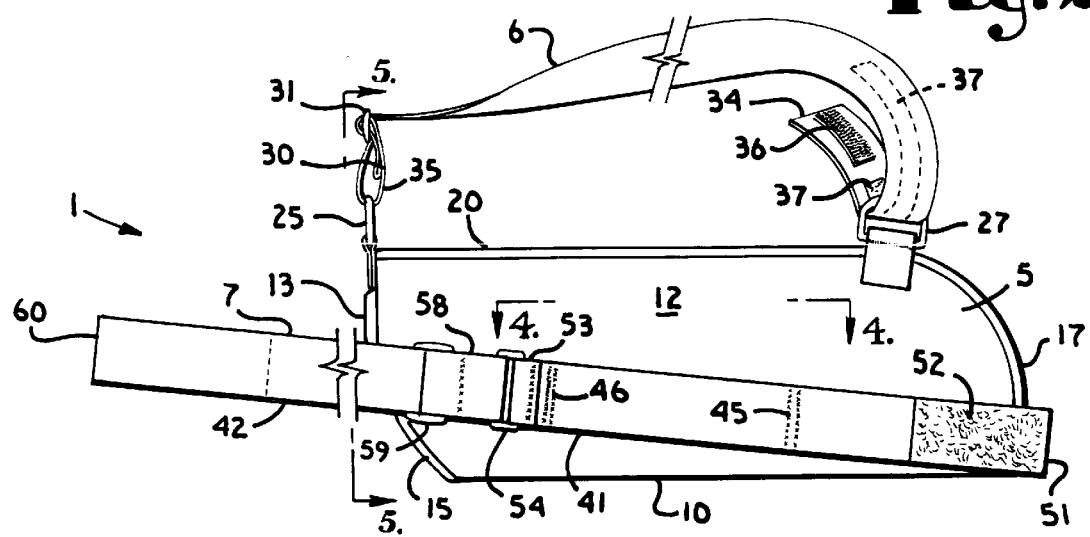
FIG. 2 is fragmentary rear elevational view of the arm sling of the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 refers to an arm sling of the present invention. The arm sling 1 includes a sling pouch 5, a shoulder strap 6 and a restraining strap or belt 7.

The sling pouch 5 is preferably formed from a single sheet of cloth cut to shape and folded in half along what becomes a bottom edge 10 of the sling pouch 5 so as to form a first or front panel 11 and a second or back panel 12. Edges 13 of the front and back panel 11 and 12 at a first or rear end thereof are sewn together to form a closed elbow end 15 of the sling pouch 5. Edges 16 of the front and back panel 11 and 12 at a second or front end thereof opposite the closed end 15 are not sewn or otherwise secured together so as to generally form an open wrist end of the sling pouch 5. Upper edges 18 of the front and back panels 11 and 12 also are left open. A binding strip 20 is secured to the front and back panels 11 and 12 along the upper edges 18, the front edges 16 and the sewn together rear edges 13. The sling pouch 5 is preferably deeper and longer than generally available sling pouches to provide greater support for an arm.

A first D-ring or connector ring 25 is secured to the sling pouch 5 at the elbow end 15 so as to extend above the upper edges 18 of the panels 11 and 12. Second and third connector rings 26 and 27 are secured to the front and back panels 11 and 12 respectively proximate the wrist end 17 of the sling pouch 5 so as to extend above the upper edges 18 thereof.

The shoulder strap 6 is formed from webbing such as nylon webbing or a relatively flexible strap material which provides support without cutting into the neck. A first end 30 of the shoulder strap 6 is generally secured to the sling pouch 5 proximate the elbow end 15. In particular, the first end 30 of the shoulder strap 6 is threaded through and wrapped around a first buckle 31 and sewn back onto itself to secure the buckle 31 thereto. A second end 34 of the shoulder strap 6 is then threaded through the first connector ring 25 and then back through the buckle 31 to form an adjustable loop 35, generally at the first end 30 of the shoulder strap 6 which is connected to the connector ring 25.

A first portion 36 of a hook and loop type fastener is secured to the shoulder strap 6 proximate the second end 34 of the shoulder strap 6 and on one side thereof. A second portion 37 of a hook and loop type fastener is secured to the shoulder strap 6 inward from the second end 36 thereof but proximate the first portion 36 and on the same side of the shoulder strap 6 as the first portion 36.

After a wearer's arm is positioned in the sling pouch 5, the second end 34 of the shoulder strap 6 is pulled over the wearer's shoulder opposite the elbow end 15 of the pouch 5 and threaded through the second and third connector rings 26 and 27. The second end 34 is then folded back onto itself and secured in place by pressing the first and second portions 36 and 37 of the hook and loop type fastener together thereby generally securing the second end 34 to the sling pouch 5 proximate the wrist end 17. The first portion of hook and loop type fastener 36 is preferably relatively short and the second portion 37 is preferably relatively long to allow the wearer to quickly adjust the length of the shoulder strap between the first connector ring 25 and the second and third connector rings 26 and 27 by adjusting the degree to which the second end 34 of the strap 6 overlaps upon itself. Similarly, the length of the shoulder strap 6 between the first connector ring 25 and the second and third connector rings 26 and 27 may be adjusted by adjusting the size of the loop formed by threading the shoulder strap 6 through the buckle 31.

The restraining strap 7 is preferably formed from two sections or lengths of webbing, a first section 41 and a second section 42. The first section 41 is secured to the back panel 12 of the sling pouch 5 by a first and second set of stitches 45 and 46 and generally extends across the back panel 12. The first section 41 is preferably angled slightly upward, from the wrist end 17 to the elbow end 15 of the sling pouch 5 from between zero to fifteen degrees and preferably approximately five degrees relative to the bottom edge 10. The first section 41 of the restraining strap 7 is secured to the back panel 12 at the slight angle such that when the sling pouch 5 is secured to the wearer by the restraining strap 7, as discussed below, the forearm is supported in a slight upwardly angled orientation, which is provides a more natural and comfortable orientation for supporting the forearm.

A first end 51 of the first section 41 has a first portion 52 of a hook and loop type fastener secured thereto. A second end 53 of the first section 41 is threaded through and wrapped around a connector ring 54 and sewn back onto itself for securing the connector ring 54 thereto. As best seen in FIG. 3, a first end 58 of the second section 42 of the restraining strap 7 is threaded through and wrapped around a center post (not shown) of a buckle 59 and sewn back onto itself for securing the buckle 59 thereto. A second end 60 of the second section 42 is threaded through the connector ring 54 on the first end 51 of the first section 41 and then through the buckle 59 and away therefrom so as to form a loop and such that the effective length of the second section 42 of the restraining strap 7 is adjustable. A second portion 61 of hook and loop type fastener is secured to the second end 60 of the second section 42 of the restraining strap 7.

The restraining strap 7 is secured intermediate its ends 51 and 60 to the back panel 12 of the sling pouch 5 inward from the elbow end 15 and wrist end 16 and generally laterally relative to the back panel 12 such that a portion of the restraining strap 7 overlaps a portion of the back panel 12.

With the wearer's arm in the sling pouch 5, the wearer generally grasps the second end 60 of the second section 42 of the restraining strap 7 and wraps the restraining strap 7 around his or her waist, generally from the elbow end 15 of the sling pouch 5 to the wrist end 17. The wearer then presses the second end 60 of the second section 42 against the first end 51 of the first section 41 such that the first and second portions 52 and 61 of hook and loop type fastener matingly engage and hold the restraining strap 7 in place and secure the pouch 5 generally against the wearer's abdomen. The first and second portions 52 and 61 of hook and loop type fastener are sufficiently long to permit adjustments to the fit of the restraining strap 7. Further, the buckle 59 allows the effective length of the restraining strap 7 to be adjusted.

The degree to which the forearm is angled upward from the elbow to the wrist, while supported in the sling pouch 5 may be adjusted by adjusting the effective length of the shoulder strap 6. In particular, the wrist end 17 of the sling pouch 5 may be generally raised against the restraint of the restraining strap 7, by increasing the degree to which the second end 34 of the shoulder strap 6 is overlapped back onto itself.

As shown in FIG. 3, the first set of stitches 45 is positioned inward from the wrist end 17 to be generally aligned with the point where the front part of the forearm including the wrist begins to separate from the abdomen against which the arm is secured, thereby allowing the portion of the sling pouch 5 extending around that portion of the arm to extend freely away from the wearer's body. The restraining strap 7 thereby does not place uncomfortable strain upon the front portion of the forearm extending away from the body.

Similarly, the second set of stitches 46 is positioned inward from the elbow end 15 to be generally aligned with the point where the rear part of the forearm including the elbow begins to separate from the abdomen against which the arm is secured, thereby allowing the portion of the sling pouch 5 extending around that portion of the arm to extend freely away from the wearer's body. The restraining strap 7 thereby does not place uncomfortable strain upon the rear portion of the forearm extending away from the body.

In the preferred embodiment, the portion of the first section 41 of the restraining strap 7 between the first and second set of stitches 45 and 46 is not fastened to the back panel 12 as generally shown in FIG. 4. In addition, the first section 41 is sewn to the back panel 12 such that the portion of the first section 41 between the set of stitches 45 and 46 is slightly longer, approximately one eighth to one quarter of an inch, than the portion of the back panel 12 across which it extends. Such a configuration provides for a more comfortable fit when snugly secured to the wearer, in part because it is believed that the cloth from which the back panel 12 of the sling pouch 5 is formed tends to stretch when pulled taught against the curvature of the abdomen while the webbing, from which the restraining strap 7 is formed, does not.

The overall design of the arm sling 1 permits the sling 1 to be put on with minimal or no assistance from another person. The hook and loop type fasteners are fairly easy to secure together with one hand and the shoulder strap 6 and the restraining strap 7 are positioned to facilitate donning of the sling 1.

It is foreseen that the restraining strap 7 could be secured to the back panel 12 by a wide variety of fastening means including pinning, hook and loop type fasteners, snaps, clips, adhesives, threading through slits, slots or openings (as discussed below), or other means. Further, although the restraining strap 7 of the preferred embodiment is shown secured to the panel 12 at two points or along two lines it is foreseen that the strap 7 could be secured to the panel 12 at a single point or along a single line, at more than two points or along more than two lines or across an area including the total area between the first and second sets of stitches 45 and 46.

FIGS. 6 and 7 show an alternative embodiment of an arm sling 70 of the present invention which is reversible. The arm sling 70 includes a sling pouch 71 which has a first panel 72 and a second panel 73, a shoulder strap 74 and a restraining strap 75. The sling pouch 71 includes an open wrist end 76 and a closed elbow end 77.

A first pair of slits, slots, holes or openings comprising first and second slits 80 and 81 are formed in the first panel 72 and spaced inward from the wrist end 76 and the elbow end 77. The slits 80 and 81 are sized for threading the restraining strap 75 therethrough across the first panel 72. The second slit 81, the slit closest to the elbow end 77, is positioned slightly higher than the first slit 80 such that when the restraining strap 75 is threaded through the slits 80 and 81 the restraining strap 75 is angled upward relative to a bottom edge 83 of the sling pouch 71 from the wrist end 76 to the elbow end 77. As noted above, the restraining strap 75 is preferably angled from between zero and fifteen degrees and preferably approximately five degrees relative to the bottom edge 83.

A second pair of slits, comprising third and fourth slits 87 and 88 are formed in the second panel 73 and spaced inward from the wrist end 76 and the elbow end 77. The slits 87 and 88 are sized for threading the restraining strap 75 therethrough across the second panel 73. The fourth slit 88, the slit closest to the elbow end 77, is positioned slightly higher than the third slit 87 such that when the restraining strap 75 is threaded through the slits 87 and 88 the restraining strap 75 is angled upward relative to a bottom edge 83 of the sling pouch 71 from the wrist end 76 to the elbow end 77. As noted above, the restraining strap 75 is preferably angled from between zero and fifteen degrees and preferably approximately five degrees relative to the bottom edge 83.

The restraining strap 75 is selectively threadable through either the first pair of slits 80 and 81 or the second pair of slits 87 and 88 such that the arm sling 70 is reversible and may be used to support either arm of the wearer. Although extending the restraining strap 75 through slits 80 and 81 or 87 and 88 does not fixedly secure the restraining strap 75 to the respective panel 72 or 73, the restraining strap 75 may generally be described as secured to the panels 72 or 73 thereby.

It is to be understood that while certain forms of the present invention have been illustrated and described herein, it is not to be limited to the specific forms or arrangement of parts described and shown.

What is claimed and desired to be secured by letters patent is as follows:

1. An arm sling comprising:
   a) a sling pouch having a front panel and a back panel and an elbow end and a wrist end;
   b) a shoulder strap having a first end secured to said sling pouch proximate said elbow end and a second end secured to said sling pouch proximate said wrist end;
   c) a restraining strap adapted to be secured around the torso of a wearer, said restraining strap having a first end and a second end; said restraining strap secured intermediate said first and second ends thereof to said back panel of said sling pouch inward from said elbow and wrist ends thereof and generally laterally relative to said back panel of said sling pouch such that a portion of said restraining strap overlaps a portion of said back panel; and
   d) a fastener for releasably securing said first and second ends of said restraining strap together.

2. The arm sling as in claim 1 wherein:
   a) said restraining strap is secured to said back panel at least a first point and a second point which are spaced inward from said wrist end and said elbow end of said sling pouch.

3. The arm sling as in claim 2 wherein:
   a) said restraining strap is secured to said back panel such that said restraining strap is angled upward at a slight angle relative to a bottom edge of said sling pouch from said wrist end to said elbow end thereof.

4. The arm sling as in claim 2 wherein:
   a) said restraining strap is secured to said back panel such that said restraining strap is angled upward between approximately zero to fifteen degrees relative to a bottom edge of said sling pouch from said wrist end to said elbow end thereof.

5. The arm sling as in claim 2 wherein:
   a) a portion of the restraining strap extending between said first and second points is not secured to said back panel.

6. The arm sling as in claim 5 wherein:
   a) said portion of said restraining strap extending between said first and second points is slightly longer than the length of the back panel extending therebetween.

7. The arm sling as in claim 1 wherein:
   a) a first pair of openings is formed in said back panel in horizontally spaced apart relation and spaced inward from said elbow end and said wrist end of said sling pouch; and said restraining strap is securable to said back panel by threading said restraining strap through said first pair of openings in said back panel.

8. The arm sling as in claim 7 wherein:
   a) said front panel has a second pair of openings formed therein in horizontally spaced apart relation and spaced inward from said elbow end and said wrist end of said sling pouch; and b) said restraining strap is selectively securable, intermediate said first and second ends of said restraining strap, to said back panel or said front panel by threading said restraining strap through said first pair of openings in said back panel or said second pair of openings in said front panel.

9. The arm sling as in claim 8 wherein:

a) said second pair of openings are offset vertically relative to one another such that when said restraining strap is threaded through said second pair of openings in said front panel said restraining strap is angled upward relative to a bottom edge of said sling pouch from said wrist end to said elbow end thereof.

10. The arm sling as in claim 8 wherein:

a) said second pair of openings are offset vertically relative to one another such that when said restraining strap is threaded through said second pair of openings in said front panel said restraining strap is angled upward between approximately zero and fifteen degrees relative to a bottom edge of said sling pouch from said wrist end to said elbow end thereof.

11. The arm sling as in claim 7 wherein:

a) said first pair of openings are offset vertically relative to one another such that when said restraining strap is threaded through said first pair of openings in said back panel said restraining strap is angled upward relative to a bottom edge of said sling pouch from said wrist end to said elbow end thereof.

12. The arm sling as in claim 7 wherein:

a) said first pair of openings are offset vertically relative to one another such that when said restraining strap is threaded through said first pair of openings in said back panel said restraining strap is angled upward between approximately zero and fifteen degrees relative to a bottom edge of said sling pouch from said wrist end to said elbow end thereof.

13. An arm sling comprising:

a) a sling pouch having a front panel and a back panel and an elbow end and a wrist end;

b) a shoulder strap having a first end secured to said sling pouch proximate said elbow end and a second end secured to said sling pouch proximate said wrist end;

c) a restraining strap having a first end and a second end and secured intermediate said first and second ends thereof to said back panel of said sling pouch at a first point and a second point which are spaced inward from said elbow and wrist ends thereof and such that a portion of said restraining strap extending between said first and second points extends in overlapping relationship with said back panel but is not secured to said back panel; said restraining strap being secured to said back panel such that said restraining strap is angled upward relative to a bottom edge of said sling pouch from said wrist end to said elbow end thereof; and d) a fastener for releasably securing said first and second ends of said restraining strap together.

14. The arm sling as in claim 13 wherein:

a) said restraining strap is secured to said back panel such that said restraining strap is angled upward between approximately zero to fifteen degrees relative to said bottom edge of said sling pouch from said wrist end to said elbow end thereof.

15. The arm sling as in claim 13 wherein:

a) said portion of said restraining strap extending between said first and second points is slightly longer than the length of said back panel extending therebetween.

16. An arm sling comprising:

a) a sling pouch having a front panel and a back panel and an elbow end and a wrist end;

b) a shoulder strap having a first end secured to said sling pouch proximate said elbow end and a second end secured to said sling pouch proximate said wrist end;

c) a restraining strap having a first end and a second end and secured intermediate said first and second ends of said restraining strap to said back panel of said sling pouch inward from said elbow and wrist ends thereof; said restraining strap is secured to said back panel at least a first point and a second point which are spaced inward from said wrist end and said elbow end of said sling pouch and a portion of the restraining strap extending between said first and second points is not secured to said back panel; said portion of said restraining strap extending between said first and second points is slightly longer than the length of the back panel extending therebetween; and d) a fastener for releasably securing said first and second ends of said restraining strap together.

17. An arm sling comprising:

a) a sling pouch having a front panel and a back panel and an elbow end and a wrist end;

b) a shoulder strap having a first end secured to said sling pouch proximate said elbow end and a second end secured to said sling pouch proximate said wrist end;

c) a restraining strap having a first end and a second end and secured intermediate said first and second ends thereof to said back panel of said sling pouch at a first point and a second point which are spaced inward from said elbow and wrist ends thereof and such that a portion of the restraining strap extending between said first and second points is not secured to said back panel; said restraining strap being secured to said back panel such that said restraining strap is angled upward relative to a bottom edge of said sling pouch from said wrist end to said elbow end thereof; said portion of said restraining strap extending between said first and second points is slightly longer than the length of said back panel extending therebetween; and d) a fastener for releasably securing said first and second ends of said restraining strap together.

* * * * *